(12) United States Patent
Furuki et al.

(10) Patent No.: US 8,077,313 B2
(45) Date of Patent: Dec. 13, 2011

(54) OPTICAL MEASURING DEVICE, OPTICAL MEASURING APPARATUS AND FINE PARTICLE MEASURING APPARATUS USING OPTICAL MEASURING DEVICE

(75) Inventors: Motohiro Furuki, Tokyo (JP); Masataka Shinoda, Tokyo (JP); Shingo Imanishi, Kanagawa (JP)

(73) Assignee: Sony Corporation, Tokyo (JP)

( * ) Notice: Subject to any disclaimer, the term of this patent is extended or adjusted under 35 U.S.C. 154(b) by 518 days.

(21) Appl. No.: 12/252,639

(22) Filed: Oct. 16, 2008

(65) Prior Publication Data

US 2009/0101847 A1 Apr. 23, 2009

(30) Foreign Application Priority Data

Oct. 18, 2007 (JP) ................. P2007-271041

(51) Int. Cl.
*G01N 15/02* (2006.01)
*G01N 21/00* (2006.01)
(52) U.S. Cl. ........................ 356/335; 356/337
(58) Field of Classification Search .................. None
See application file for complete search history.

(56) References Cited

U.S. PATENT DOCUMENTS

| 6,224,732 | B1 | 5/2001 | Imasaka et al. |
| 7,578,915 | B2* | 8/2009 | Karger et al. .............. 204/451 |
| 2004/0079893 | A1 | 4/2004 | Dietz et al. |

FOREIGN PATENT DOCUMENTS

| JP | 1-92622 | 6/1989 |
| JP | 3-150445 | 6/1991 |
| JP | 7-24309 | 1/1995 |
| JP | 2002-195949 | 7/2002 |
| JP | 2002-523731 | 7/2002 |
| JP | 2003-247981 | 9/2003 |
| JP | 2006-242726 | 9/2006 |
| JP | 2006-284530 | 10/2006 |
| JP | 2007-46947 | 2/2007 |
| JP | 2007-285999 | 11/2007 |

OTHER PUBLICATIONS

Anne Y. Fu et al., "A Microfabricated Fluorescence-Activated Cell Sorter", Nature Biotechnology, Nov. 1999, pp. 1109-1111, vol. 17, Nature America Inc.

Anne Y. Fu et al., "An Integrated Microfabricated Cell Sorter", Analytical Chemistry, Jun. 1, 2002, pp. 2451-2457, vol. 74, No. 11, American Chemical Society.

English-language translation of Notification of Reasons for Refusal prepared by the Japanese Patent Office in JP 2007-271041, drafted Sep. 29, 2009.

* cited by examiner

*Primary Examiner* — Michael A Lyons
*Assistant Examiner* — Amanda Merlino
(74) *Attorney, Agent, or Firm* — Finnegan, Henderson, Farabow, Garrett & Dunner, L.L.P.

(57) ABSTRACT

Disclosed herein is an optical measuring device, including: a plurality of microfluidic channels extending in parallel to each other; and a scanning section configured to scan a plurality of measuring light beams in a scanning direction in which the microfluidic channels are juxtaposed to optically measure fine particles introduced into the microfluidic channels.

7 Claims, 7 Drawing Sheets

OPTICAL MEASURING DEVICE, OPTICAL MEASURING APPARATUS AND FINE PARTICLE MEASURING APPARATUS USING OPTICAL MEASURING DEVICE

CROSS REFERENCES TO RELATED APPLICATIONS

The present invention contains subject matter related to Japanese Patent Application JP 2007-271041 filed in the Japan Patent Office on Oct. 18, 2007, the entire contents of which being incorporated herein by reference.

BACKGROUND OF THE INVENTION

1. Field of the Invention

This invention relates to an optical measuring device, an optical measuring apparatus and a fine particle measuring apparatus which uses an optical measuring device.

2. Description of the Related Art

In the past, apparatus are known which introduce fluid dispersion of fine particles such as living body-related fine particles such as cells, microorganisms and ribosome, latex particles or gel articles and synthetic particles such as industrial particles into a microfluidic channel and optically measure the fine particles introduced in the microfluidic channel in order to discriminate the fine particles.

One of such apparatuses is a particle analyzer which discriminates various synthetic particles depending upon the size and/or the shape of the same. The particle analyzer excites fine particles one by one in helium plasma so as to emit light to carry out spectral detection thereby to carry out measurement of the element composition, particle size and particle number of the fine particles.

Further, for living-body related fine particles, optical measurement using a flow cytometry or flow cytometer is used popularly as disclosed, for example, in Hiromitsu NAKAUCHI, "Cellular Engineering Separate Volume, Experiment Protocol Series, Master Flow Cytometry," Shujunsha, the second edition, Aug. 31, 2006. According to the flow cytometry, fine particles such as cells or micro beads are flowed to the center of laminar flow of sheath liquid in a flow cell and measuring light is irradiated upon the fine particles in an optical detection section to detect scattered light or fluorescent light generated from the fine particles thereby to measure the size, structure and so forth of the fine particles.

The flow cytometry is configured so as to only measure the size, structure and so forth of fine particles or configured such that it can dispense desired fine particles based on the measured size, structure and so forth. Of such flow cytometries, that flow cytometry which dispenses cells is called "cell sorter." Cell sorters on the market are manufactured by Beckman Coulter, Inc., Becton, Dickinson and Company or DAKO S/A. With those cell sorters, high-speed measurement and dispense of several tens to hundred thousand cells per second can be carried out.

In recent years, such optical measuring apparatus for fine particles are demanded to have a further enhancement measurement process speed and further enhanced measurement accuracy. Particularly for a cell sorter described above, it is demanded to have a processing speed and a measurement accuracy for efficiently isolating stem cells, which exist only little among living body cells, in response to rise of expectations for regenerative medicine.

In connection with the invention disclosed herein, a configuration of an existing cell sorter is shown in FIGS. 7 and 8 of Japanese Patent Laid-Open No. 2007-46947 (hereinafter referred to as Patent Document 1). The cell sorter includes a fluid or flow system for arraying cells colored with fluorescence-labeled reagent into a line in a flow cell, and an optical system for irradiating a plurality of Laser beams to detect detection target light such as scattered light and fluorescent light. The optical system of the existing flow cytometer is configured such that a plurality of measuring light beams from a plurality of light sources are condensed at different positions of the flow cell which forms a single microfluidic channel (refer to the FIG. 7 of Patent Document 1).

Meanwhile, Japanese Patent Laid-Open No. Hei 7-24309 (hereinafter referred to as Patent Document 2) discloses an apparatus for separation of particles, which includes a microfluidic channel along which particles move and a section for irradiating scanning light upon the microfluidic channel such that acting force corresponding to the type of particles is applied by the irradiation to carry out separation of the particles. While this apparatus has a configuration for scanning the scanning light on the flow cell, this scanning light is used for laser trapping of particles (refer to paragraph 0004 and so forth of Patent Document 2). It is to be noted that also this apparatus has a single configuration of the flow cell serving as a microfluidic channel.

Also a technique of forming fine microfluidic channels on a substrate of glass or a high-molecular material and flowing fine particles such as cells on water streams in the fine microfluidic channels to carry out flow cytometry to separate desired fine particles, which is a technique which utilizes a microchip, has been proposed. The technique is disclosed, for example, in Anne Y. Fu, et al., "A microfabricated fluorescence-activated cell sorter," Nature Biotechnology, Vol. 17, November 1999, pp. 1109-111; or in Anne Y. Fu, et al., "An Integrated Microfabricated Cell Sorter," Analytical Chemistry, Vol. 74, No. 11, Jun. 1, 2002, pp. 2451-2457. The microchip forms T-shaped microfluidic channels and isolates cells to be dispensed and the other cells from each other by changing over the flowing direction of sheath liquid, that is, by microfluidic channel selection control.

SUMMARY OF THE INVENTION

Taking such a demand for enhancement of the measurement processing speed and the measurement accuracy of an optical measuring apparatus for fine particles as described above into consideration, it is desirable to provide an optical measuring device and an optical measuring apparatus which achieve a superior measurement processing speed and superior measurement accuracy and a fine particle measuring apparatus which includes the optical measuring device.

According to an embodiment of the present invention, there is provided an optical measuring device including a plurality of microfluidic channels extending in parallel to each other, and a scanning section for scanning a plurality of measuring light beams in a scanning direction in which the microfluidic channels are juxtaposed to optically measure fine particles introduced into the microfluidic channels.

Preferably, the scanning section scans the measuring light beams such that, when one of the measuring light beams is irradiated upon one of the microfluidic channels, the other measuring light beams are not irradiated upon any one of the microfluidic channels.

In this instance, preferably the optical measuring device is configured such that the microfluidic channels are arranged in a predetermined spaced relationship from each other in the scanning direction while the measuring light beams are irradiated and scanned in such a manner as to be spaced from each other at distances in the scanning direction, and where the microfluidic channel width of the microfluidic channels in the scanning direction is represented by $w_{channel}$, a minimum distance D[min] from among the distances between two adjacent ones of the measuring light beams in the scanning direction and a spot width W of the measuring light beams satisfy the following expression (1):

$$w_{channel} + W < D(\min) \tag{1}$$

In this instance, further preferably the optical measuring device is configured such that, where the distance between the microfluidic channels in the scanning direction is represented by $d_{channel}$, a number N of the measuring light beams, a maximum distance D(max) in the scanning direction between two adjacent measuring light beams selected from the measuring light beams and the spot width W of the measuring light beams satisfy the following expression (2):

$$D(\max) \times (N-1) + W < d_{channel} \tag{2}$$

Alternatively, the optical measuring device may be configured such that the microfluidic channels are arranged in a predetermined spaced relationship from each other in the scanning direction while the measuring light beams are irradiated and scanned in such a manner as to be spaced from each other at distances in the scanning direction, and where each of the distances between the microfluidic channels in the scanning direction is divided into a plurality of zones of a predetermined dimension in the scanning direction, each of the measuring light beams is irradiated in one of the zones and one of the zones in which one of the measuring light beams is irradiated and another one of the zones in which another one of the measuring light beams is irradiated are different from each other and are not continuous to each other.

In the optical measuring device, scanning of the measuring light beams can be carried out such that, where one of the measuring light beams is irradiated upon one of the microfluidic channels, the other measuring light beams are not irradiated upon any one of the microfluidic channels.

The microfluidic channels may be disposed on an exchangeable member.

In particular, according to another embodiment of the present invention, there is provided an optical measuring apparatus including an exchangeable member, and an optical measuring device including a plurality of microfluidic channels extending in parallel to each other and a scanning section for scanning a plurality of measuring light beams in a scanning direction in which the microfluidic channels are juxtaposed to optically measure fine particles introduced into the microfluidic channels, the microfluidic channels being arranged in a predetermined spaced relationship from each other in the scanning direction while the measuring light beams are irradiated and scanned in such a manner as to be spaced from each other at distances in the scanning direction, the microfluidic channels having a microfluidic channel width w in the scanning direction which satisfies the following expression (3):

$$w + W_{spot} < D_{spot}(\min) \tag{3}$$

where $W_{spot}$ is a spot width of the measuring light beams in the scanning direction and $D_{spot}(\min)$ is a minimum distance from among the distances between two ones of the measuring light beams in the scanning direction.

Preferably, the optical measuring apparatus is configured such that, where the number of the measuring light beams is represented by $N_{\lambda ex}$ and a maximum one of the distances between two adjacent ones of the measuring light beams in the scanning direction is represented by D(max), a distance d between the microfluidic channels in the scanning direction satisfies the following expression (4):

$$D_{spot}(\max) \times (N_{\lambda ex} - 1) + W_{spot} < d \tag{4}$$

According to a further embodiment of the present invention, there is provided an optical measuring apparatus including an exchangeable member, and an optical measuring device including a plurality of microfluidic channels extending in parallel to each other and a scanning section for scanning a plurality of measuring light beams in a scanning direction in which the microfluidic channels are juxtaposed to optically measure fine particles introduced into the microfluidic channels, the microfluidic channels being arranged in a predetermined spaced relationship from each other in the scanning direction while the measuring light beams are irradiated and scanned in such a manner as to be spaced from each other at distances in the scanning direction, each of the measuring light beams being irradiated, where each of the distances between the microfluidic channels in the scanning direction is divided into a plurality of zones of a predetermined dimension in the scanning direction, in one of the zones while one of the zones in which one of the measuring light beams is irradiated and another one of the zones in which another one of the measuring light beams is irradiated are different from each other and are not continuous to each other.

In the optical measuring apparatus, scanning of the measuring light beams can be carried out such that, where one of the measuring light beams is irradiated upon one of the microfluidic channels, the other measuring light beams are not irradiated upon any one of the microfluidic channels.

According to a still further embodiment of the present invention, there is provided a fine particle measuring apparatus including an optical measuring device including a plurality of microfluidic channels extending in parallel to each other and a scanning section for scanning a plurality of measuring light beams in a scanning direction in which the microfluidic channels are juxtaposed to optically measure fine particles introduced into the microfluidic channels.

It is to be noted that, in the expressions (1) to (4) given above, the alphabetical letters "W, D, N, w, d" represent variables, and the alphabetical letters with a suffix "$w_{channel}$, $d_{channel}$, $W_{spot}$, $D_{spot}$, $N_{\lambda ex}$" represent arbitrary constants. Further, the capital letters "W, D, N, $W_{spot}$, $D_{spot}$, $N_{\lambda ex}$" represent numerical values which define the conditions to be satisfied by the measuring light beams, and the small letters "w, d" represent numerical letters which define the conditions to be satisfied by the microfluidic channels.

Also it is to be noted that the "fine particle measuring apparatus" may be applied widely as apparatus for optically measuring fine particles such as living body-related fine particles such as cells, microorganisms and ribosome, latex particles or gel articles and synthetic particles such as industrial particles, including such a particle analyzer, a flow cytometer and a cell sorter as described hereinabove.

In summary, the present invention provide an optical measuring device and an optical measuring apparatus which achieve a superior measurement processing speed and superior measurement accuracy and a fine particle measuring apparatus which includes the optical measuring device.

The above and other objects, features and advantages of the present invention will become apparent from the following description and the appended claims, taken in conjunction with the accompanying drawings in which like parts or elements denoted by like reference symbols.

DETAILED DESCRIPTION OF THE PREFERRED EMBODIMENT

Figure 1:
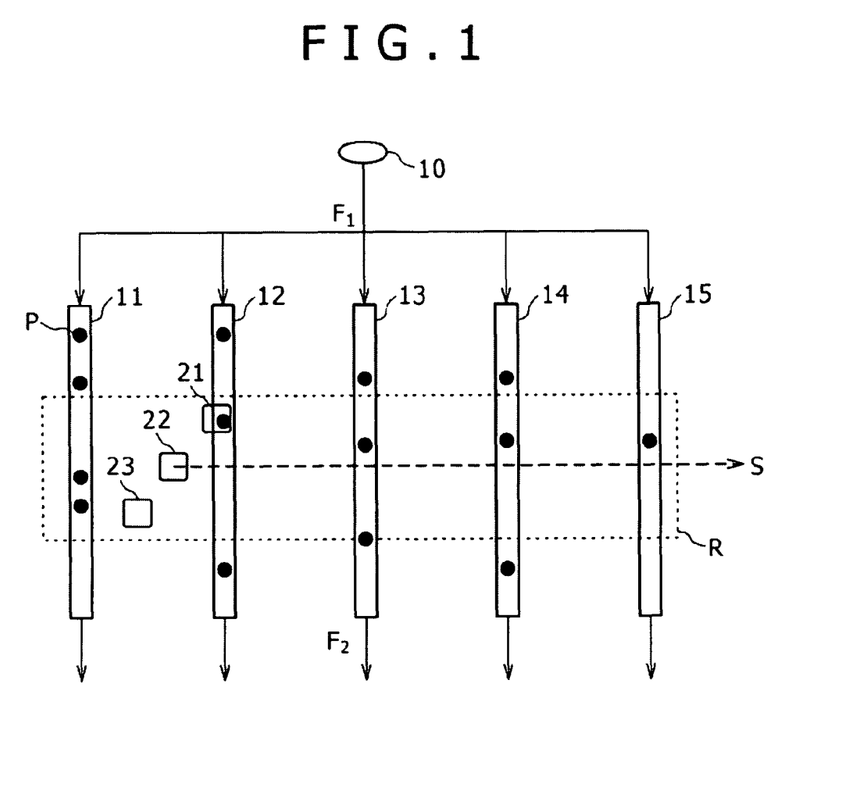
FIG. 1 is a schematic view illustrating arrangement of microfluidic channels and a scanning direction of measuring light beams in an optical measuring device to which an embodiment of the present invention is applied.

Referring first to FIG. 1, there are shown arrangement of microfluidic channels and a scanning direction of measuring light beams on an optical measuring device to which an embodiment of the present invention is applied.

The optical measuring device includes microfluidic channels 11, 12, 13, 14 and 15 into which fine particles P can be introduced. The microfluidic channels 11 to 15 are arrayed at predetermined distances in a scanning direction, which is indicated by a broken line arrow mark S, of measuring light beams hereinafter described and extend in parallel to each other in a direction perpendicular to the scanning direction. It is to be noted that FIG. 1 shows a configuration of the microfluidic channels at a portion of the optical measuring device in the proximity of an irradiation region R of the measuring light beams while the other portion of the microfluidic channels is omitted. Further, while FIG. 1 shows a configuration wherein five microfluidic channels are arranged, the number of microfluidic channels is not limited to this, but may be any arbitrary number equal to or greater than 2.

Dispersing solvent of fine particles P can be supplied, for example, from a specimen reserving section 10 and distributed so as to be introduced into the microfluidic channels 11 to 15. Gaseous or liquid solvent is used as the dispersing solvent suitably in response to the fine particles P of a target of measurement.

When the solvent is introduced into the microfluidic channels 11 to 15, the fine particles P are arrayed one by one into each of the microfluidic channels 11 to 15 by a flow system not shown. The flow system includes a nozzle for forwarding the dispersing solvent containing the fine particles P usually as a laminar flow and another nozzle for forwarding only the solvent as a laminar flow. The two nozzles cooperate to form a laminar flow of the fine particles P at the center of the solvent laminar flow or sheath flow. Further, when the dispersing solvent of the fine particles P is forwarded, a small pressure difference is applied between the nozzles so that the fine particles P are arrayed one by one in the laminar flow. Consequently, the fine particles P are arrayed and fed one by one at the center of each of the microfluidic channels 11 to 15.

The fine particles P arrayed one by one in each of the microfluidic channels 11 to 15 are fed in the direction indicated by an arrow mark $F_1$ from the upstream side of the microfluidic channel, that is, from the upper side in FIG. 1. Thus, after the fine particles P pass a measuring light irradiation region R, they are fed in the direction indicated by an arrow mark $F_2$ to the downstream side which is the lower side in FIG. 1.

Measuring light beams 21, 22 and 23 are used for optical measurement of the fine particles P. The measuring light beams 21 to 23 are irradiated upon the fine particles P arrayed in the microfluidic channels 11 to 15 in the measuring light irradiation region R. Thereupon, the measuring light beams 21 to 23 are scanned in the direction indicated by a broken line arrow mark S so as to be irradiated upon the fine particles P arrayed in the microfluidic channels 11 to 15. It is to be noted that, while FIG. 1 shows the configuration wherein three light beams are used for irradiation, the number of measuring light beams is not limited as far as an expression (2) hereinafter given is satisfied, and any number of measuring light beams equal to or greater than 2 may be used.

Optical measurement of the fine particles P can be carried out by detecting detection target light such as scattered light and fluorescent light which are generated from the fine particles P by irradiation of the measuring light beams by means of a detector not shown. Thereupon, in the optical measuring device according to the embodiment of the present embodiment, the measuring light beams are scanned such that, when one measuring light beam is irradiated upon one microfluidic channel, none of the other measuring light beams is irradiated upon the other microfluidic channels. For example, in FIG. 1, when the measuring light beam 21 is irradiated upon the microfluidic channel 12, the measuring light beams 22 and 23 are not irradiated upon any microfluidic channel. This can be achieved by arranging the microfluidic channels at predetermined distances in a juxtaposed relationship in the scanning direction of the measuring light beams and irradiating and scanning the measuring light beams at predetermined distances. In the following, particular examples of the arrangement distances of the microfluidic channels and the irradiation distances of the measuring light beams are described with reference to FIGS. 2A to 5.

Figure 2A:
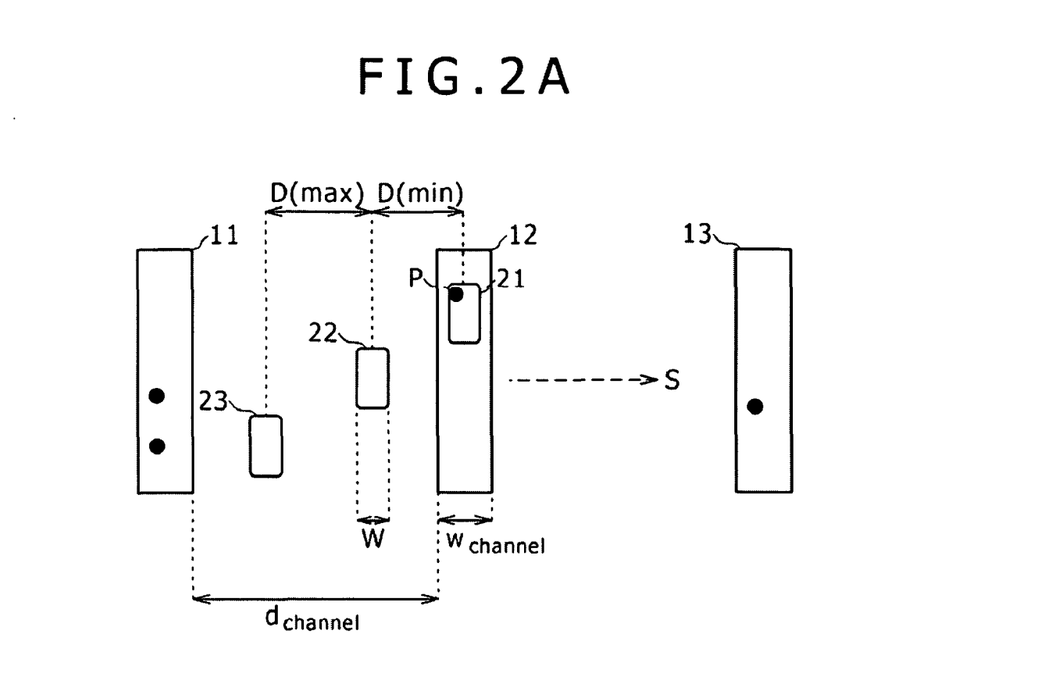
FIGS. 2A and 2B are schematic views illustrating arrangement distances of the microfluidic channels and irradiation distances of the measuring light beams in the optical measuring device.
Figure 2B:
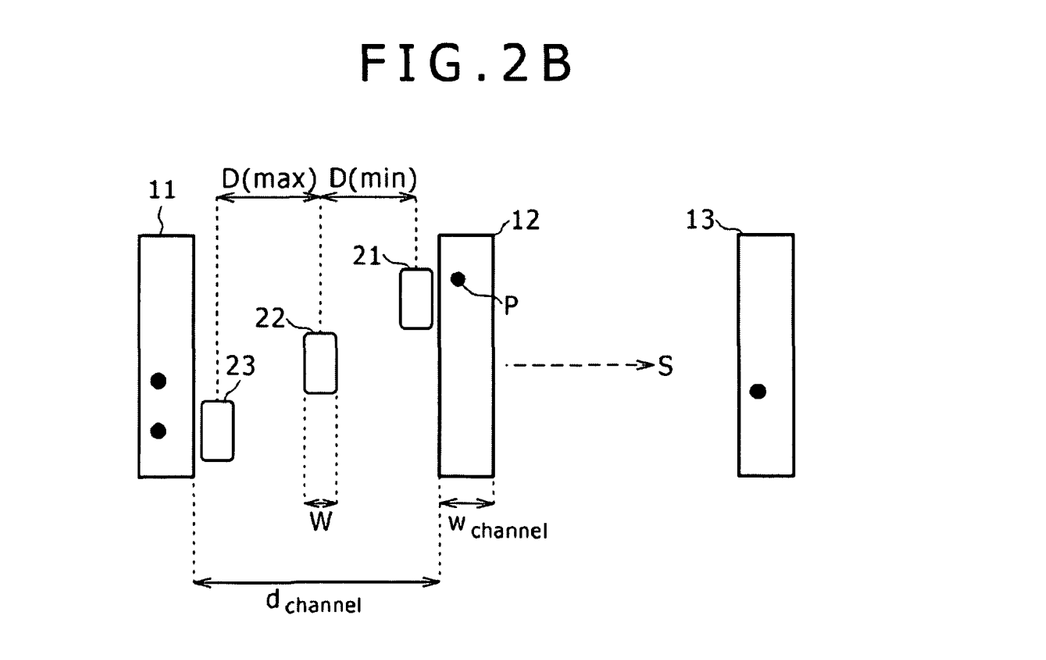
Figure 3:
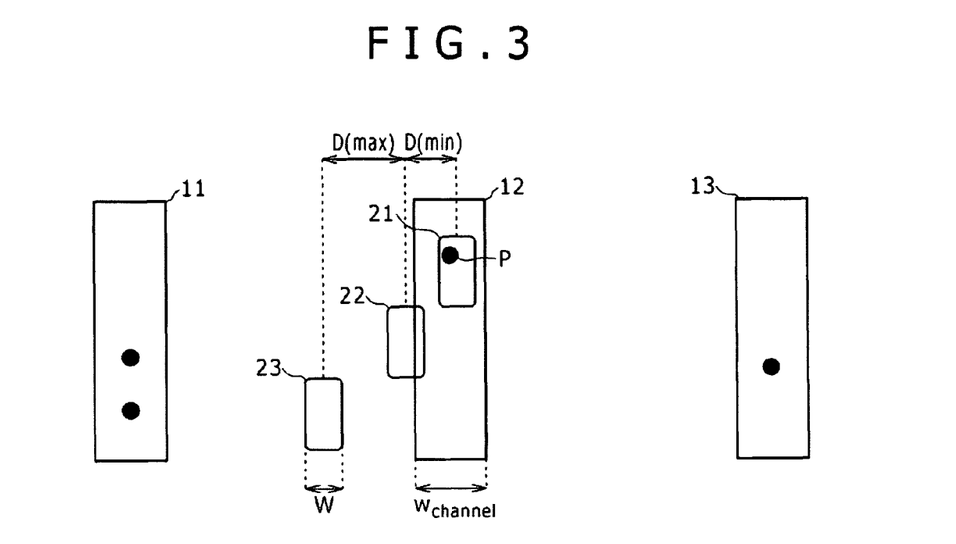
FIGS. 3 to 5 are schematic views illustrating different examples of inappropriate arrangement distances of the microfluidic channels and inappropriate irradiation distances of the measuring light beams in the optical measuring device.
Figure 4:
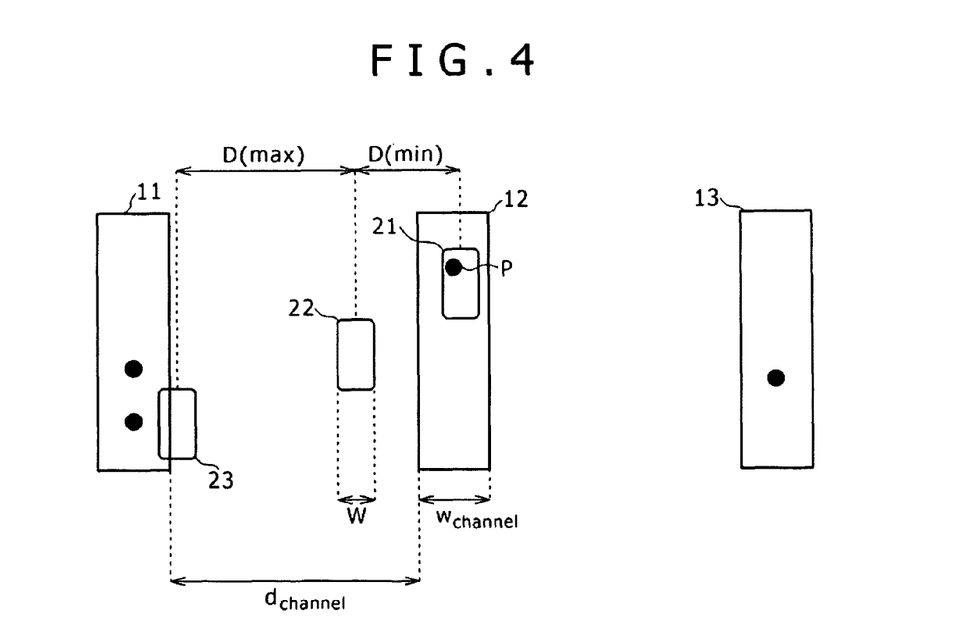
Figure 5:
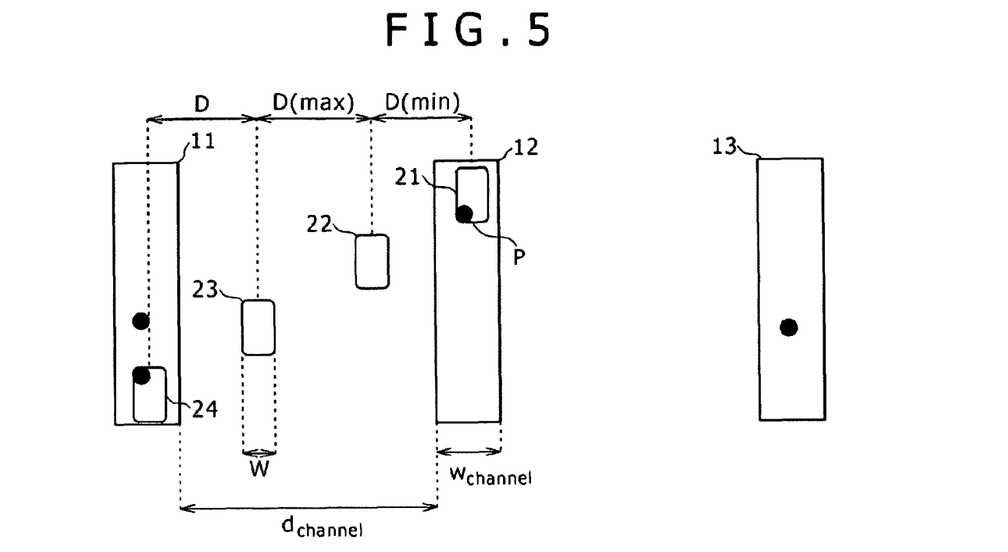

FIGS. 2A and 2B illustrate the arrangement distances of the microfluidic channels and the irradiation distances of the measuring light beams in the optical measuring device to which the embodiment of the present invention is applied. On the other hand, FIGS. 3 to 5 illustrate arrangement distances of the microfluidic channels and irradiation distances of the measuring light beams which are inappropriate to the optical measuring device according to the embodiment of the present invention.

FIGS. 2A and 2B show the measuring light irradiation region R of the microfluidic channels 11 to 13 shown in FIG. 1 and the measuring light beams 21 to 23 in an enlarged scale. The microfluidic channels 11 to 13 have a microfluidic channel width $w_{channel}$ in the scanning direction, indicated by a broken line arrow mark S in FIGS. 2A and 2B, of the measuring light beams, and adjacent ones of the microfluidic channels 11 to 13, that is, the microfluidic channels 11 and 12 and the microfluidic channels 12 and 13, are spaced away from each other by a microfluidic channel distance or land width $d_{channel}$. Further, the measuring light beams 21 to 23 have a spot width W in the scanning direction thereof, and adjacent ones of the measuring light beams 21 to 23, that is, the measuring light beams 21 and 22 and the measuring light beams 22 and 23, are spaced away from each other by an irradiation distance D.

Now, two conditions to be satisfied by the two variables or parameters of the spot width W and the irradiation distance D of the measuring light beams where the microfluidic channel width $w_{channel}$ and the microfluidic channel distance $d_{channel}$ are arbitrary constants are described in regard to the arrangement distances of the microfluidic channels and the irradiation distances of the measuring light beams in the optical measuring device according to the present embodiment.

First, the spot width W and the irradiation distance D have to satisfy the following expression (1):

$$w_{channel} + W < D(\min) \quad (1)$$

where D(min) represents a minimum distance in the scanning direction S between two adjacent measuring light beams selected from the measuring light beams 21 to 23, that is, the distance between the measuring light beams 21 and 22 or the distance between the measuring light beams 22 and 23. In FIGS. 2A and 2B, the distance between the measuring light beams 21 and 22 is the irradiation distance D(min).

In particular, the irradiation distance D(min) is set greater than the sum of the microfluidic channel width $w_{channel}$ and the spot width W. In other words, it is necessary for the measuring light beams to be irradiated in a spaced relationship from each other by a distance greater than the sum of the microfluidic channel width $w_{channel}$ and the spot width W. Consequently, as seen in FIG. 2A, when the measuring light beam 21 is irradiated upon the microfluidic channel 12, the measuring light beam 22 is prevented from being irradiated upon the microfluidic channel 12 simultaneously.

FIG. 3 illustrates an alternative configuration for comparison wherein the irradiation distance D(min) is smaller than the sum of the microfluidic channel width $w_{channel}$ and the spot width W. In this instance, since the irradiation distance D(min) between the measuring light beams 21 and 22 is small and may not satisfy the expression (1) given hereinabove, when the measuring light beam 21 is irradiated upon the microfluidic channel 12, the measuring light beam 22 is irradiated on the microfluidic channel 12 simultaneously. Thus, the configuration that "while one measuring light beam is irradiated upon one microfluidic channel, the other measuring light beams are not irradiated upon any microfluidic channel" is not implemented.

The spot width W and the irradiation distance D satisfy also the following expression (2):

$$D(\max) \times (N-1) + W < d_{channel} \quad (2)$$

where N is the number of measuring light beams. In FIGS. 2A and 2B, three measuring light beams 21 to 23 are illustrated, and therefore, N=3. Meanwhile, D(max) represents a maximum distance in the scanning direction S between two adjacent measuring light beams selected from the measuring light beams 21 to 23, that is, the distance between the measuring light beams 21 and 22 or between the measuring light beams 22 and 23. In FIGS. 2A and 2B, the distance between the measuring light beams 22 and 23 is the irradiation distance D(max).

In particular, the sum of the product of the irradiation distance D(max) and the number of measuring light beams decremented by 1 and the spot width W is set smaller than the microfluidic channel distance $d_{channel}$. In other words, it is necessary for the measuring light beams to be irradiated in such a spaced relationship from each other that the irradiation positions of all measuring light beams are included in the microfluidic channel distance or land width $d_{channel}$. Consequently, such a configuration that, when the measuring light beam 21 is irradiated, the measuring light beam 23 is prevented from being simultaneously irradiated upon the microfluidic channel 12 as seen in FIG. 2A can be implemented.

For comparison, alternative configurations wherein the sum of the product of the irradiation distance D(max) and the number of measuring light beams decremented by 1 and the spot width W is greater than the microfluidic channel distance $d_{channel}$ are shown in FIGS. 4 and 5. Referring first to FIG. 4, in the configuration shown, the irradiation distance D(max) is so large that the expression (2) given above is not satisfied, and therefore, when the measuring light beam 21 is irradiated upon the microfluidic channel 12, the measuring light beam 23 is irradiated on the microfluidic channel 11 simultaneously. On the other hand, in FIG. 5, the number of measuring light beams (N=4) is so great that the expression (2) is not satisfied, and therefore, when the measuring light beam 21 is irradiated upon the microfluidic channel 12, the measuring light beam 24 is irradiated on the microfluidic channel 11 similarly. Accordingly, in both of FIGS. 4 and 5, the configuration that "where one measuring light beam is irradiated upon one microfluidic channel, the other measuring light beams are not irradiated upon any microfluidic channel" is not implemented.

While, in the configuration of the optical measuring device, the microfluidic channel width $w_{channel}$ and the microfluidic channel distance $d_{channel}$ can be set to arbitrary values, in this instance, if the spot width W and the irradiation distance D of the measuring light beams are formed so as to satisfy the expressions (1) and (2) given hereinabove in response to the numerical values of the microfluidic channel width $w_{channel}$ and the microfluidic channel distance $d_{channel}$, then it is possible for only one measuring light beam to be normally irradiated upon only one microfluidic channel.

It is to be noted that conditions to be satisfied by the microfluidic channel width $w_{channel}$ and the microfluidic channel distance $d_{channel}$ of the microfluidic channels where the spot width W and the irradiation distance D of the measuring light beams are set to arbitrary values in the configuration of the optical measuring device are hereinafter described with reference to FIG. 10.

The arrangement distances of the microfluidic channels and the irradiation distances of the measuring light beams shown in FIGS. 2A and 2B can be defined in the following manner.

Figure 6:
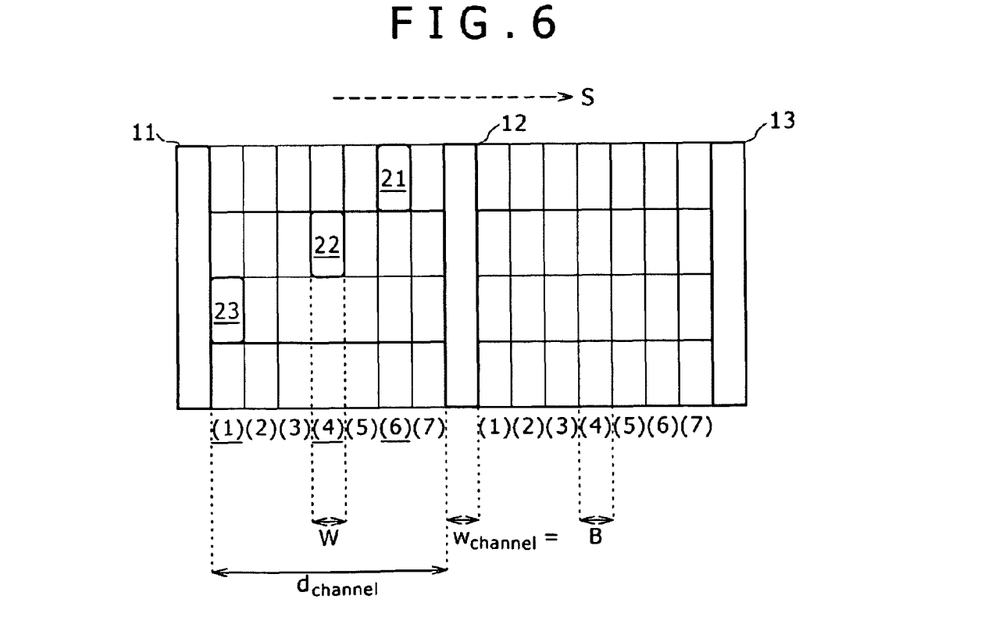
FIGS. 6 and 7A to 7C are schematic views illustrating different examples of the arrangement distances of the microfluidic channels and the irradiation distances of the measuring light beams in the optical measuring device.

FIG. 6 illustrates arrangement distances of microfluidic channels and irradiation distances of measuring light beams in the optical measuring device to which the embodiment of the present invention is applied. It is to be noted that fine particles P are not shown in FIG. 6. This similarly applies also to FIG. 7.

In particular, FIG. 6 shows the measuring light irradiation region R of the microfluidic channels 11 to 13 in FIG. 1 and the measuring light beams 21 to 23 in an enlarged scale. The microfluidic channels 11 to 13 have the microfluidic channel width $w_{channel}$ in the scanning direction, indicated by a broken line arrow mark S in FIG. 6, of the measuring light beams, and adjacent ones of the microfluidic channels 11 to 13, that is, the microfluidic channels 11 and 12 and the microfluidic channels 12 and 13, are spaced away from each other by the microfluidic channel distance $d_{channel}$. Further, the measuring light beams 21 to 23 have the spot width W in the scanning direction thereof.

Each microfluidic channel distance or land width $d_{channel}$ is divided into a plurality of zones having a predetermined width in the scanning direction S. In particular, the land width $d_{channel}$ is divided into zones (1) to (7) having a zone width B in FIG. 6 equal to the microfluidic channel width $w_{channel}$.

The measuring light beams 21 to 23 are irradiated upon some different ones of the zones (1) to (7) as seen in FIG. 6. Further, the zones upon which the measuring light beams are irradiated are not continuous to each other.

In particular, the measuring light beam 23 is irradiated upon the zone (1); the measuring light beam 22 is irradiated upon the zone (4); and the measuring light beam 21 is irradiated upon the zone (6). In FIG. 6, the number of each zone upon which a measuring light beam is irradiated is indicated by an underline. It is to be noted that, while, in FIG. 6, the spot width W of the measuring light beams is shown equal to the band width B, it may be set arbitrarily if it does not exceed the band width B.

Further, the zones (1), (4) and (6) upon which the measuring light beams are irradiated are all different from each other and are not continuous to each other. Here, that the zones are not continuous to each other signifies that the numbers (1), (4) and (6) of the zones are discontinuous to each other.

By the configuration described above, the microfluidic channels 11 to 13 are configured such that "where one measuring light beam is irradiated upon one microfluidic channel, the other measuring light beams are not irradiated upon any microfluidic channel."

In particular, since the distance between the measuring light beam 21 and the measuring light beam 22 and the distance between the measuring light beam 22 and the measuring light beam 23 are at least greater than the one-zone width, such a situation that the measuring light beam 21 and the measuring light beam 22 are irradiated simultaneously upon the same microfluidic channel or the measuring light beam 22 and the measuring light beam 23 are irradiated simultaneously upon the same microfluidic channel does not occur (refer to FIG. 3).

Further, since the measuring light beams 21 to 23 are irradiated in such a spaced relationship from each other that they are included in the microfluidic channel distance or land distance $d_{channel}$, such a situation that, while the measuring light beam 21 is irradiated upon the microfluidic channel 12, the measuring light beam 23 is irradiated upon the microfluidic channel 11, for example, as seen in FIG. 4 does not occur.

Figure 7A:
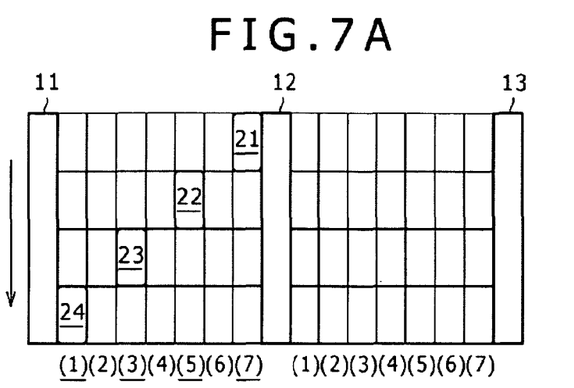
Figure 7B:
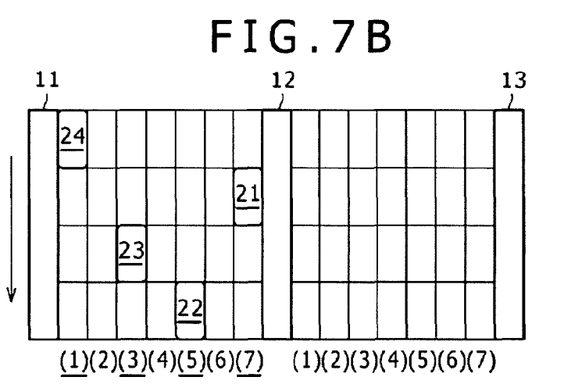

Naturally, it is possible to dispose four or more measuring light beams as seen in FIG. 7A if the condition that the measuring light beams are irradiated in different ones of the zones (1) to (7) which are not continuous to each other is satisfied. Further, the irradiation positions of the measuring light beams in the microfluidic channel flowing direction (refer to an arrow mark in FIG. 7B) can be set arbitrarily. This is hereinafter described in detail with reference to FIG. 8.

Figure 7C:
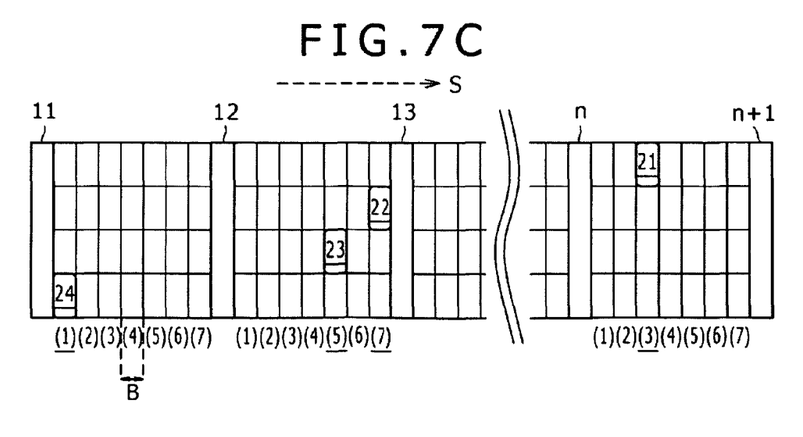

Also it is possible to adopt a different configuration wherein measuring light beams are irradiated upon a plurality of different portions between microfluidic channels, that is, upon lands.

Referring to FIG. 7C, each land is divided into zones having a zone width (refer to reference character B) equal to the microfluidic channel width $w_{channel}$ and having zone numbers (1) to (7) applied thereto. In this instance, a measuring light beam 24 is irradiated upon the zone (1) in a region between the microfluidic channel 11 and the microfluidic channel 12, that is, upon the land 1. The measuring light beam 23 and the measuring light beam 22 are irradiated upon the zone (5) and the zone (7) between the microfluidic channel 12 and the microfluidic channel 13, that is, upon the land 2. Further, the measuring light beam 21 is irradiated upon the zone 3 in a region between the microfluidic channel n and the microfluidic channel n+1, that is, upon the land n. In FIG. 7C, the number of each zone upon which a measuring light beam is irradiated is indicated by an underline.

The measuring light beams are irradiated upon different zones (1), (3), (5) and (7) whose zone numbers are discontinuous to each other.

Consequently, also where measuring light beams are irradiated upon portions between a plurality of different microfluidic channels, that is, upon lands, the microfluidic channels can be configured such that "where one measuring light beam is irradiated upon one microfluidic channel, the other measuring light beams are not irradiated upon any microfluidic channel" similarly as in the case wherein the measuring light beams are irradiated upon the same portion between microfluidic channels.

In this manner, with the optical detecting device to which the present embodiment is applied, since fine particles of a target of measurement are introduced into a plurality of microfluidic channels and measuring light beams are scanned to carry out optical measurement of the fine particles introduced in the microfluidic channels, it is possible to complete the measuring process in a short period of time when compared with that of an existing optical measuring device wherein a measuring light beam is irradiated upon a fixed point of the single microfluidic channel to carry out measurement.

Further, since a measuring light beam is always irradiated only upon one microfluidic channel, such a situation that detection target light is generated simultaneously from fine particles in a plurality of microfluidic channels, and high measurement accuracy can be achieved.

In particular, otherwise if, while one measuring light beam is irradiated upon one microfluidic channel, some other measuring light beam is irradiated upon some microfluidic channel, then detection target light is generated from fine particles in a plurality of different microfluidic channels, resulting in occurrence of interference or crosstalk of the detection target light. Such crosstalk gives rise to a drop of the accuracy in measurement, and in order to eliminate this, it is necessary to provide detectors individually for different microfluidic channels such that detection target light generated from fine particles in the microfluidic channels is detected individually.

In contrast, in the optical measuring device of the present embodiment, since one measuring light beam is always irradiated only upon one microfluidic channel, crosstalk of detection target light does not occur, and high measurement accuracy can be obtained. Further, since detection target light is always generated from one microfluidic channel, the detection target light can be detected by a single detector, and consequently, the optical system can be significantly simplified in configuration.

Further, in the optical measuring device of the present embodiment, preferably the measuring light beams scan in a displaced relationship from each other in the feeding direction (refer to arrow marks $F_1$ and $F_2$ in FIG. 1) of fine particles P in the microfluidic channels as seen in FIGS. 1, 2A and 2B. This is described with reference to FIGS. 8A and 8B.

Figure 8A:
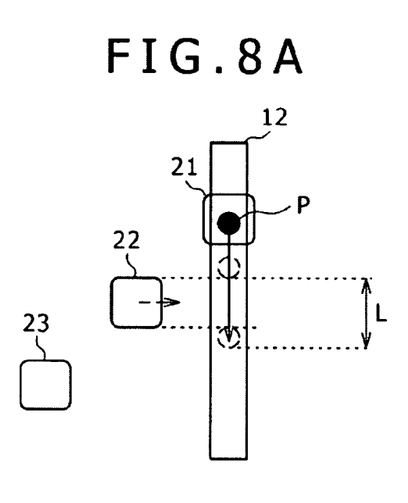
FIGS. 8A and 8B are schematic views illustrating irradiation positions of the measuring light beams in a microfluidic channel flowing direction.
Figure 8B:
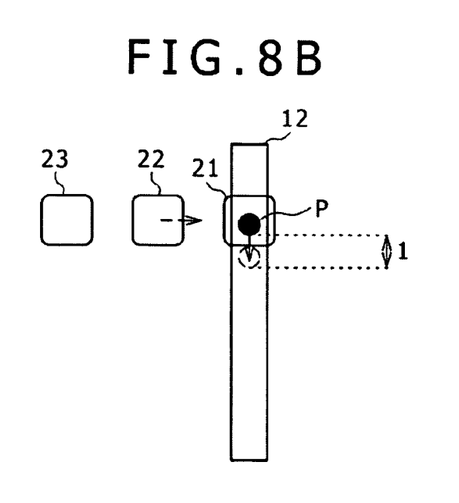

FIGS. 8A and 8B show an irradiation position of a measuring light beam in the microfluidic channel feeding direction. In FIGS. 8A and 8B, a solid line arrow mark indicates the microfluidic channel feeding direction, and a broken line arrow mark indicates the scanning direction of the measuring light beam. FIGS. 8A and 9b illustrate a state wherein the measuring light beam 21 is irradiated upon a fine particle P in the microfluidic channel 12.

In the state illustrated in FIG. 8A, the fine particle P measured with the measuring light beam 21 is subsequently measured with the measuring light beam 22. In this instance, the fine particle P is fed at a predetermined speed in the microfluidic channel 12 and thus moves in the direction indicated by the solid line arrow mark in FIG. 8A.

Here, if the measuring light beams 21 to 23 are arrayed otherwise on a linear line in the scanning direction, that is, in the direction indicated by the broken line arrow mark in FIG. 8B to carry out scanning, then it is necessary to carry out measurement with the measuring light beam 22 at the same position as the position at which the measurement is carried out with the measuring light beam 21.

More particularly, in FIG. 8B, it is necessary to scan the measuring light beam 22 on the microfluidic channel 12 to carry out measurement with the measuring light beam 22 before the fine particle P is fed by a distance l. Therefore, depending upon the feeding speed of the fine particle P, there is the possibility that measurement with the measuring light beam 22 may not be carried out successfully.

Also where the measuring light beam 23 and four or more measuring light beams are used, it is necessary to scan each measuring light beam on the microfluidic channel 12 before the fine particle P is fed by the distance l similarly, and depending upon the feeding speed of the fine particle P, there is the possibility that measurement with all of the measuring light beams may not be carried out successfully.

In contrast, since, in FIG. 8A, the measuring light beams 21 to 23 are scanned in a displaced relationship from each other in the microfluidic channel feeding direction, measurement with the measuring light beam 22 can be carried out on the downstream of the microfluidic channel 12 from measurement with the measuring light beam 21. In particular, if the measuring light beam 22 is scanned on the microfluidic channel 12 before the fine particle P is fed by a distance L (L>l), then measurement of the fine particle P with the measuring light beam 22 can be carried out. Here, since it is possible to set the distance L greater than the distance l, with the configuration of the present embodiment, measurement with the measuring light beam 22 can be carried out in higher accuracy.

Further, also where the measuring light beam 23 and four or more measuring light beams are used, measurement may be carried out on the further downstream side of the microfluidic channel 12 similarly, and measurement with all of the measuring light beams can be carried out with a high degree of accuracy.

With the optical measuring device to which the present embodiment is applied, each microfluidic channel has at least one of an inlet for introducing fine particles and another inlet for introducing and controlling a solvent laminar flow or sheath flow. The sectional shape of the microfluidic channels may be a rectangular shape, a circular shape, an elliptic shape or the like. The microfluidic channels are formed from a material such as quartz or a plastic material such as PP, PC, COP or PDMS which can transmit a measuring light beam therethrough and exhibits a comparatively small wavelength dispersion and a comparatively small optical error with respect to a measuring light beam. The inner surface of the microfluidic channels is formed as a processed surface which can maintain a formed laminar flow. Further, the microfluidic channels may be disposed in a fixed state or may be disposed on an exchangeable member such as a substrate A hereinafter described.

The fine particles P include living body-related fine particles such as cells, microorganisms, living body high-molecular substance, latex particles or gel particles, synthetic particles such as industrial particles. The cells include animal cells such as blood type cells and plant cells. The microorganisms include bacteria such as colon bacilli, viruses such as tobacco mosaic viruses, fungi such as yeast fungi. The living body high-molecular substance includes chromosome, ribosome, mitochondria and organelle. The industrial particles may be formed, for example, from an organic or inorganic high-molecular material, a metal or the like. The organic high-molecular material includes polystyrene, styrene-divinylbenzene and polymethyl methacrylate. The inorganic high-molecular material includes glass, silica and a magnetic material. The metal includes gold colloid and aluminum. Although such fine particles as mentioned above normally have a spherical shape, they may otherwise have an aspherical shape, and also the size, mass and so forth of them are not limited particularly.

Further, the measuring light beams may have waveforms selected from among various waveforms in accordance with the type of the fine particles P of a measurement target and the target of measurement. Also the light source may be selectively used suitably from known light sources such as a gas laser such as an argon laser or a helium laser, a semiconductor laser (LD), a light emitting diode (LED) and so forth.

For example, for the object of measuring an elementary composition of the fine particles P, measuring light beams of wavelengths corresponding to absorption wavelengths of the individual elements is selectively used. On the other hand, where fluorescent light of fine particles labeled with a plurality of fluorescent dyes is to be measured, measuring light beams of wavelengths corresponding to excitation wavelengths of the individual fluorescent dyes are used. For example, if wavelengths of 405, 473 and 658 nm are used for the measuring light beams 21, 22 and 23 in FIG. 1, respectively, then three different fluorescent dyes individually having the wavelengths as excitation wavelengths thereof can be used to carry out discrimination of the fine particles P.

Scanning of measuring light beams is carried out on a fixed cycle using a polygon mirror, a galvano mirror, an acousto-optical element, an electro-optical element or the like disposed on a light path of a measuring light beam emitted from each of the light sources of the different wavelengths. The irradiation system for each measuring light beam is formed as a telecentric optical system so that the spot width of the measuring light beam may be fixed on an image formation plane on the corresponding microfluidic channel.

As described hereinabove, in the optical measuring device to which the present invention is applied, each of the microfluidic channels may be disposed on an exchangeable member, and for the optical measuring member, the optical measuring member disclosed in non-patent documents by Anne Y. Fu, et al. mentioned hereinabove wherein very small microfluidic channels are formed on a substrate of glass or a high-molecular material can be adopted suitably. Where such a substrate as just mentioned is used, the problem of mixture of impurities or contamination arising from repeated use of a flow cell or microfluidic channel and appearing in an existing optical measuring device can be solved.

Figure 9:
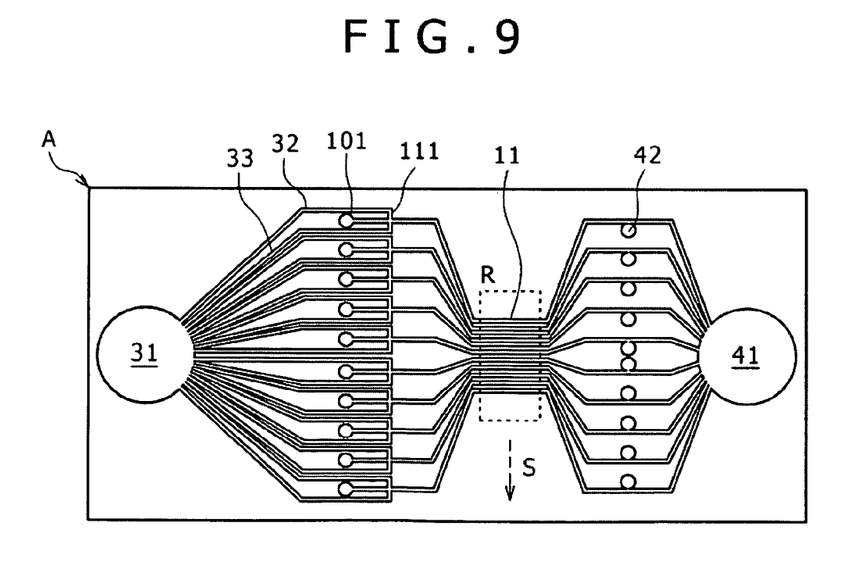
FIG. 9 is a top plan view showing an example of an optical measuring apparatus or substrate to which the embodiment of the present invention is applied.

FIG. 9 shows an example of an optical measuring apparatus which is in the form of a substrate.

Referring to FIG. 9, ten microfluidic channels into which fine particles can be introduced are formed on a substrate A. One of the microfluidic channels is denoted by reference numeral 11. In the following, a configuration of the microfluidic channel 11 is described. However, also the other microfluidic channels have a similar configuration. It is to be noted that the number of microfluidic channels is not limited particularly but may be arbitrarily set to any number equal to or greater than 2.

Dispersed solvent of fine particles P not shown in FIG. 9 is introduced into the microfluidic channel 11 from a specimen introducing portion 101. A solvent introduction portion 31 is provided at one end of the microfluidic channel 11, and the solvent introduced from the solvent introduction portion 31 is fed to solvent feeding paths 32 and 33 of the microfluidic channel 11 and joins the dispersed solvent of the fine particles P introduced from the specimen introducing portion 101 at a confluence portion 111. Thereupon, the solvent which joins from the solvent feeding paths 32 and 33 serves as a sheath flow and plays a role of arraying the fine particles P one by one to the center in the microfluidic channel 11. It is to be noted that the dispersed solvent of the fine particles P is thrown in, for example, from the specimen stock section 10 shown in FIG. 1 and branches to specimen introducing portions 101 of the microfluidic channels (also refer to arrow mark $F_1$ in FIG. 1).

The fine particles P arrayed one by one in the microfluidic channel 11 are fed into the measuring light irradiation region R, in which they are measured with the measuring light beams scanned in the direction indicated by a broken line arrow mark S in FIG. 9. While the arrangement distances of the microfluidic channels and the irradiation distances of the measuring light beams are such as described hereinabove with reference to FIGS. 2A to 5, conditions to be satisfied by two variables or parameters of the microfluidic channel width w and the microfluidic channel distance d of the microfluidic channels on a substrate where the spot width $W_{spot}$ and the irradiation distance $D_{spot}$ of the measuring light beams are set to arbitrary values paying attention to conditions to be satisfied by the substrate A side are described.

Figure 10:
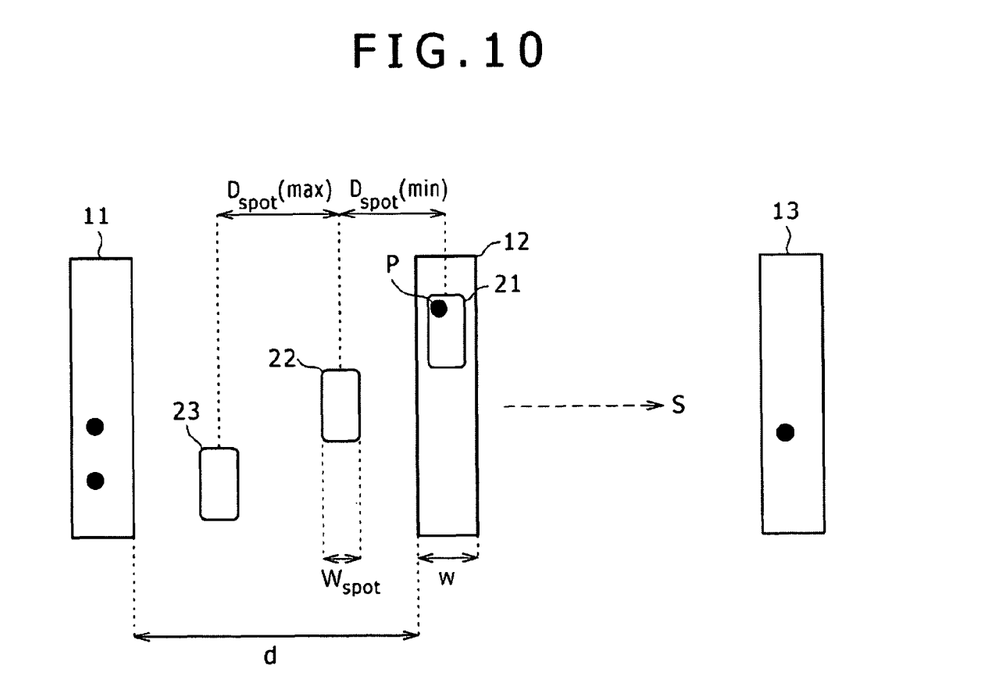
FIG. 10 is a schematic view illustrating arrangement distances of microfluidic channels and irradiation distances of measuring light beams on the optical measuring apparatus or substrate.

FIG. 10 illustrates arrangement distances of microfluidic channels and irradiation distances of measuring light beams in the optical measuring apparatus or substrate to which the present embodiment is applied.

FIG. 10 shows the measuring light irradiation region R shown in FIG. 9 in an enlarged scale. In FIG. 10, three microfluidic channels 11 to 13 are shown as representatives and three measuring light beams are used similarly as in FIGS. 2A to 5.

Referring to FIG. 10, the spot width of the measuring light beams 21 to 23 in the scanning direction thereof indicated by a broken line arrow mark S is represented by $W_{spot}$, and the irradiation distance between adjacent ones of the measuring light beams, that is, between the measuring light beams 21 and 22 or between the measuring light beams 22 and 23, is represented by $D_{spot}$. Further, the width of the microfluidic channels 11 to 13 in the broken line arrow mark S is represented by w, and the distance, that is, the land width, between adjacent ones of the microfluidic channels, that is, between the microfluidic channels 11 and 12 or between the microfluidic channels 12 and 13, is represented by d.

First, the microfluidic channel width w of the microfluidic channels satisfies the following expression (3):

$$w+W_{spot}<D_{spot}(\min) \quad (3)$$

where $D_{spot}(\min)$ is a minimum distance from among the distances in the scanning direction S between two adjacent measuring light beams selected from among the measuring light beams 21 to 23, that is, from between the distance between the measuring light beams 21 and 22 and the distance between the measuring light beams 22 and 23. In FIG. 10, the distance between the measuring light beams 21 and 22 is the irradiation distance $D_{spot}(\min)$.

In particular, the spot width w is set such that the sum thereof with the spot width $W_{spot}$ is smaller than the irradiation distance $D_{spot}(\min)$. In other words, it is necessary for the microfluidic channels to be formed in a spaced relationship from each other by a distance smaller than the difference of the spot width $W_{spot}$ from the irradiation distance $D_{spot}(\min)$.

Further, the microfluidic channel distance d satisfies the following expression (4):

$$D_{spot}(\max)\times(N_{\lambda ex}-1)+W_{spot}<d \quad (4)$$

where N is the number of measuring light beams. In FIG. 10, three measuring light beams 21 to 23 are illustrated, and therefore, N=3. Meanwhile, $D_{spot}(\max)$ represents a maximum distance in the scanning direction S between two adjacent measuring light beams selected from among the measuring light beams 21 to 23, that is, the distance between the measuring light beams 21 and 22 or between the measuring light beams 22 and 23. In FIG. 10, the distance between the measuring light beams 22 and 23 is the irradiation distance $D_{spot}(\max)$.

In particular, the microfluidic channel distance d is set greater than the value of the sum of the product of the irradiation distance $D_{spot}(\max)$ and the number of measuring light beams decremented by 1 and the spot width $W_{spot}$. In other words, it is necessary for the microfluidic channels to be formed in such a spaced relationship from each other that the irradiation positions of all measuring light beams are included in the microfluidic channel distance or land width d.

Here, while the upper limit value to the microfluidic channel distance d is not set particularly, the microfluidic channel distance d is set to a suitable value with reference to the magnitudes of the irradiation distance $D_{spot}(\max)$ and the spot width $W_{spot}$ of the measuring light beams and the magnitude of the substrate itself. More particularly, the size of the substrate A shown in FIG. 9 is approximately 70 mm long× approximately 30 mm broad, and each of the microfluidic channels is provided in a region of approximately 6 mm in each direction on the substrate A. In FIG. 9, the microfluidic channels are shown large with respect to the entire substrate. Accordingly, the magnitude of the microfluidic channel distance d supposed normally is approximately 350 to 500 μm and does not exceed 1 mm in the maximum.

While, in the configuration of the measuring light beams, the spot width $W_{spot}$ and the irradiation distance $D_{spot}$ of the measuring light beams can be set to arbitrary values, in this instance, the microfluidic channel width w of the substrate and the microfluidic channel distance d are set so as to satisfy the expressions (3) and (4) given hereinabove in accordance with the values of the spot width $W_{spot}$ and the irradiation distance $D_{spot}$ so that only one measuring light beam is normally irradiated upon only one microfluidic channel similarly as described hereinabove with reference to FIGS. 2A to 5.

Further, it is possible to adopt such a configuration that, similarly as in the case described hereinabove with reference to FIG. 6, the measuring light beams 21 to 23 are irradiated upon some different ones of a plurality of zones into which each microfluidic channel distance is divided so as to have a predetermined width in the scanning direction S and the zones are not continuous to each other. By this, the microfluidic channels can be configured such that "where one measuring light beam is irradiated upon one microfluidic channel, the other measuring light beams are not irradiated upon any microfluidic channel."

In this manner, with the optical detecting apparatus or substrate according to the present embodiment, since fine particles of a target of measurement are introduced into a plurality of microfluidic channels and measuring light beams are scanned to carry out optical measurement of the fine particles introduced in the microfluidic channels, it is possible to complete the measuring process in a short period of time when compared with that of an existing substrate on which a single microfluidic channel is provided while a measuring light beam is irradiated upon a fixed point of the single microfluidic channel to carry out measurement.

Further, since a measuring light beam is always irradiated upon only one microfluidic channel, crosstalk of a target of detection does not occur. Consequently, high measurement accuracy can be achieved, and detection target light can be detected by a single detector.

The substrate A is formed from a material such as glass or a plastic material such as PP, PC, COP or PDMS which can transmit a measuring light beam therethrough and exhibits a comparatively small wavelength dispersion and a comparatively small optical error with respect to a measuring light beam. Where the material of the substrate A is glass, microfluidic channels are transferred by wet etching or dry etching. On the other hand, where the material of the substrate A is a plastic material, microfluidic channels are formed on a substrate by nanoimprint or molding. The microfluidic channels of the substrate on which the microfluidic channels are formed are sealed with a cover using the same material as that of the substrate.

Now, a scanning method of measuring light beams and a detection method of detection target light by the optical measuring device and a fine particle measuring apparatus in which the optical measuring device is arranged are described below with reference to FIG. 9 taking a case wherein the substrate A is arranged as an example.

The measuring light beams and the light source as well as the scanning system may be suitably and selectively used in accordance with the fine particles P of a target of measurement and the target of the measurement as described hereinabove. Here, the fine particle measuring apparatus is described wherein laser diodes (LDs) having wavelengths of 405, 473 and 658 nm are used as the light sources and such light measuring light beams from the light sources are scanned to discriminate the fine particles P depending upon three different fluorescent dyes individually having the wavelengths as excitation wavelengths thereof. It is to be noted that detection target light is not limited to fluorescent light but may be scattered light such as forwardly scattered light for measuring the size of measurement target fine particles, sidewardly scattered light for measuring the structure, scattered light by Rayleigh scattering or Mie scattering, or the like. Further, the fluorescent light may be any of coherent fluorescent light and incoherent fluorescent light.

The discrimination described below of fine particles P in which a plurality of fluorescent dyes described below are used is adopted suitably where a popular flow cytometer is used to discriminate cells or living body high molecules labeled with fluorescent dyes. The discrimination is used also for discrimination of micro beads containing fluorescent dyes.

First, the fine particles P arrayed one by one in the microfluidic channel 11 are fed into the measuring light irradiation region R, in which the measuring light beams of the wavelengths of 405, 473 and 658 nm which are scanned in the direction indicated by the broken line arrow mark S in FIG. 9 are irradiated. Thereupon, if a fine particle P is labeled with a fluorescent dye whose excitation wavelength is one of the above-specified wavelengths, then fluorescent light, that is, detection target light, is emitted from the fine particle P. Here, since the fine particles P are labeled with the three different fluorescent dyes, fluorescent light generated by irradiation of three different measuring light beams exhibits 2×2×2=8 patterns based on whether or not light is emitted from each fluorescent dye. The fine particles P can be discriminated by analyzing a fluorescent light pattern generated from the fine particles P.

Fluorescent light generated from any of the fluorescent dyes whose excitation wavelengths are 405, 473 and 658 nm upon irradiation of measuring light beams is scattered, for example, by a grating and then detected for each wavelength using a multi-channel photo multiplier tube (PMT). The PMT amplifies and converts detected light of any wavelength into an electric signal and outputs the electric signal to a data analysis section provided in the apparatus.

Thereupon, since the microfluidic channels of the substrate A and the measuring light beams are configured so as to satisfy the expressions (1) to (4) given hereinabove, one of the measuring light beams scanned by the polygon mirror is always irradiated upon only one of the microfluidic channels. Therefore, fluorescent light is generated only from one microfluidic channel, and fluorescent light is not generated from any other microfluidic channel simultaneously. Accordingly, even if a single detector is used to detect fluorescent light, no crosstalk occurs, and high measurement accuracy can be obtained. Further, where the apparatus is formed using a single detector, the structure of the optical measuring device and the fine particle measuring apparatus can be simplified.

With the fine particle measuring apparatus to which the present embodiment is applied, a population or group which indicates a predetermined fluorescent pattern can be dispensed based on the fluorescent pattern of the fine particle P.

After the measurement in the measuring light irradiation region R, the fine particle P is discharged to the outside of the microfluidic channel 11 from the specimen discharging section 41 in FIG. 9. At this time, a dispensing portion 42 provided between the measuring light irradiation region R and the specimen discharging portion 41 dispenses a desired group from among the fine particles P.

The data analysis section provided in the apparatus receives an output of an electric signal from the PMT to discriminate a fluorescent pattern of each fine particle P and outputs a dispense signal regarding the fine particle P which indicates a predetermined fluorescent pattern to the dispensing portion 42. The dispensing portion 42 dispenses, based on the dispense signal, a group of those of the fine particles P fed in the microfluidic channel 11 which indicate the predetermined fluorescent pattern.

The dispensing portion 42 may be formed based on the known technique disclosed, for example, in non-patent documents by Anne Y. Fu, et al. mentioned hereinabove, or an ultrasonic wave generation element disclosed in Japanese Patent Laid-Open No. 2004-85323 or a gel electrode disclosed in Japanese Patent Laid-Open No. 2006-220423 (refer to claim 10) may be used. According to the method which uses the gel electrode, by supplying predetermined current to two gel electrodes made of gel containing electrolyte and disposed in an opposing relationship to each other on the opposite sides of a microfluidic channel and in a displaced relationship from each other in the feeding direction of solvent, the microfluidic channel to which a fine particle P is to be fed is changed over thereby to dispense a desired group.

As described above, in the optical measuring device and the fine particle measuring apparatus to which the present embodiment is applied, by introducing fine particles of a target of measurement into a plurality of microfluidic channels to carry out measurement or dispense, it is possible to complete the measuring process in a short period of time when compared with that of an existing substrate on which a single microfluidic channel is provided while a measuring light beam is irradiated upon a fixed point of the single microfluidic channel to carry out measurement or dispense.

The optical measuring device according to the embodiment of the present invention can be utilized for optical measurement of fine particles such as living-body related fine particles such as cells, microorganisms and ribosome, latex particles or gel articles and synthetic particles such as industrial particles.

Further, the optical measuring apparatus and the fine particle measuring apparatus can be utilized as a flow cytometry or a particle analyzer.

It should be understood by those skilled in the art that various modifications, combinations, sub-combinations and alterations may occur depending on design requirements and other factor in so far as they are within the scope of the appended claims or the equivalents thereof.

What is claimed is:

1. An optical measuring device, comprising:
a plurality of microfluidic channels extending in parallel to each other, wherein said microfluidic channels are arranged in a predetermined spaced relationship from each other in the scanning direction while the measuring light beams are irradiated and scanned in such a manner as to be spaced from each other at distances in the scanning direction, and where the microfluidic channel width of said microfluidic channels in the scanning direction is represented by $w_{channel}$, a minimum distance D(min) from among the distances between two adjacent ones of the measuring light beams in the scanning direction and a spot width W of the measuring light beams satisfy the following expression (1):

$$w_{channel} + W < D(\min) \tag{1}; \text{ and}$$

scanning means for scanning a plurality of measuring light beams in a scanning direction in which said microfluidic channels are juxtaposed to optically measure fine particles introduced into said microfluidic channels,
wherein said scanning means scans the measuring light beams such that, when one of the measuring light beams is irradiated upon one of said microfluidic channels, the other measuring light beams are not irradiated upon any one of said microfluidic channels.

2. The optical measuring device according to claim 1, wherein, where the distance between said microfluidic channels in the scanning direction is represented by dchannel, a number N of the measuring light beams, a maximum distance D(max) in the scanning direction between two adjacent measuring light beams selected from the measuring light beams and the spot width W of the measuring light beams satisfy the following expression (2):

$$D(\max) \times (N-1) + W < d_{channel} \tag{2}.$$

3. The optical measuring device according to claim 1, wherein said microfluidic channels are arranged in a predetermined spaced relationship from each other in the scanning direction while the measuring light beams are irradiated and scanned in such a manner as to be spaced from each other at distances in the scanning direction, and where each of the distances between said microfluidic channels in the scanning direction is divided into a plurality of zones of a predetermined dimension in the scanning direction, each of the measuring light beams is irradiated in one of the zones and one of the zones in which one of the measuring light beams is irradiated and another one of the zones in which another one of the measuring light beams is irradiated are different from each other and are not continuous to each other.

4. The optical measuring device according to claim 1, wherein said microfluidic channels are disposed on an exchangeable member.

5. An optical measuring apparatus, comprising:
an exchangeable member; and
an optical measuring device including a plurality of microfluidic channels extending in parallel to each other and scanning means for scanning a plurality of measuring light beams in a scanning direction in which said microfluidic channels are juxtaposed to optically measure fine particles introduced into said microfluidic channels;
said microfluidic channels being arranged in a predetermined spaced relationship from each other in the scanning direction while the measuring light beams are irradiated and scanned in such a manner as to be spaced from each other at distances in the scanning direction;
said microfluidic channels having a channel width w in the scanning direction which satisfies the following expression (3):

$$w + W_{spot} < D_{spot}(\min) \tag{3}$$

where $W_{spot}$ is a spot width of the measuring light beams in the scanning direction and $D_{spot}(\min)$ is a minimum distance from among the distances between two ones of the measuring light beams in the scanning direction.

6. The optical measuring apparatus according to claim 5, wherein, where the number of the measuring light beams is represented by $N\lambda ex$ and a maximum one of the distances between two adjacent ones of the measuring light beams in the scanning direction is represented by D(max), a distance d between said microfluidic channels in the scanning direction satisfies the following expression (4):

$$D_{spot}(\max) \times (N_{\lambda ex} - 1) + W_{spot} < d \tag{4}.$$

7. An optical measuring apparatus, comprising:
an exchangeable member; and
an optical measuring device including a plurality of microfluidic channels extending in parallel to each other and scanning means for scanning a plurality of measuring light beams in a scanning direction in which said microfluidic channels are juxtaposed to optically measure fine particles introduced into said microfluidic channels;
said microfluidic channels being arranged in a predetermined spaced relationship from each other in the scanning direction while the measuring light beams are irradiated and scanned in such a manner as to be spaced from each other at distances in the scanning direction;
each of the measuring light beams being irradiated, where each of the distances between said microfluidic channels in the scanning direction is divided into a plurality of zones of a predetermined dimension in the scanning direction, in one of the zones while one of the zones in which one of the measuring light beams is irradiated and another one of the zones in which another one of the measuring light beams is irradiated are different from each other and are not continuous to each other.

* * * * *